United States Patent [19]
Edgren et al.

[11] Patent Number: 5,200,194
[45] Date of Patent: Apr. 6, 1993

[54] ORAL OSMOTIC DEVICE

[75] Inventors: David E. Edgren, El Granada; Gurdish K. Bhatti, Fremont, both of Calif.

[73] Assignee: ALZA Corporation, Palo Alto, Calif.

[21] Appl. No.: 809,741

[22] Filed: Dec. 18, 1991

[51] Int. Cl.$^5$ .............................................. A61K 9/24
[52] U.S. Cl. ............................... 424/473; 424/468; 424/472
[58] Field of Search .................... 424/473, 472, 468

[56] References Cited

U.S. PATENT DOCUMENTS

| | | | |
|---|---|---|---|
| 2,799,241 | 7/1957 | Wurster | 118/24 |
| 3,133,132 | 5/1964 | Loeb et al. | 264/49 |
| 3,173,876 | 3/1965 | Zobrist | 252/137 |
| 3,276,586 | 10/1966 | Rosaen | 210/90 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,845,770 | 11/1974 | Theeuwes et al. | 128/260 |
| 3,916,899 | 11/1975 | Theeuwes et al. | 128/260 |
| 4,111,202 | 9/1978 | Theeuwes | 128/260 |
| 4,160,020 | 7/1979 | Ayer et al. | 424/15 |
| 4,327,725 | 5/1982 | Cortese et al. | 128/260 |
| 4,568,535 | 2/1986 | Loesche | 428/435 |
| 5,021,053 | 6/1991 | Barclay et al. | 604/890.1 |

Primary Examiner—Thurman K. Page
Assistant Examiner—Leon R. Horne
Attorney, Agent, or Firm—Jean M. Duvall; D. Byron Miller; Steven F. Stone

[57] ABSTRACT

An osmotic device (10) for delivering a beneficial drug, such as an anti-microbial drug, into the mouth of a human patient is disclosed. The device (10) has a size and shape adapting it to be comfortably retained in the mouth for extended periods of time. The device comprises a thin semipermeable membrane wall (12) surrounding a compartment (13) housing a beneficial agent (14) that has at least some degree of solubility in aqueous biological fluids, e.g., saliva, and a fibrous support material (15) composed of hydrophilic water-insoluble fibers. A passageway (17) in the wall (12) connects the agent 14) with the exterior of the device (10). The wall (12) is permeable to the passage of aqueous biological fluid but substantially impermeable to the passage of the fibrous support material (15). The fibrous support material (15), once hydrated, provides a rigid support for the thin semipermeable wall (12) and prevents the device (10) from prematurely releasing the beneficial agent (14) even when the device (10) is subjected to patient sucking.

19 Claims, 1 Drawing Sheet

ORAL OSMOTIC DEVICE

TECHNICAL FIELD

This invention pertains to an osmotic device for delivering a beneficial agent into the oral cavity of a patient. More particularly, the invention relates to an osmotic device comprising a shaped semipermeable wall surrounding a compartment containing a beneficial agent that is insoluble to very soluble in an aqueous fluid. A passageway through the wall connects the exterior of the device with the compartment containing the beneficial agent for delivering the agent from the device into the oral cavity.

BACKGROUND ART

Osmotic devices for delivering a beneficial agent to an environment of use are disclosed in Theeuwes et al. U.S. Pat. Nos. 3,845,770 and 3,916,899. These osmotic devices include a semipermeable wall that surrounds a compartment containing an agent. The wall is permeable to the passage of an external fluid, and substantially impermeable to the passage of agent. There is a passageway through the wall for delivering the agent from the device. These devices release agent by fluid being imbibed through the wall into the compartment at a rate determined by the permeability of the wall and the osmotic pressure gradient across the wall to produce an aqueous solution containing agent that is dispensed through the passageway from the device. These devices are extraordinarily effective for delivering an agent that is soluble in the fluid and exhibits an osmotic pressure gradient across the wall against the fluid, and for delivering an agent that has limited solubility in the fluid and is admixed with an osmotically effective compound that is soluble in the fluid and exhibits an osmotic pressure gradient across the wall against the fluid. Devices of this type can be swallowed in in order to deliver the agent throughout the transit of the device through the gastrointestinal (GI) tract. Alternatively, devices of his type can be implanted to deliver a drug or other beneficial agent to the body.

In U.S. Pat. No. 4,111,202, the delivery kinetics of the device are enhanced by manufacturing the device with an agent compartment and an osmagent compartment separated by a film, which film is movable from a rested to an expanded state. The device delivers agent by fluid being imbibed through the wall into the osmagent compartment producing a solution that causes the compartment to increase in volume and act as a driving force that is applied against the film. This force urges the film to expand against the agent compartment and correspondingly diminish the volume of this compartment, whereby agent is dispensed through the passageway from the device. While this device operates successfully for its intended use, and while it can deliver numerous difficult to deliver agents, its use is somewhat limited because of the manufacturing steps needed for fabricating and placing the movable film in the device.

In U.S. Pat. No. 4,327,725 Cortese et al provided an osmotic dispensing device for delivering a beneficial agent which, because of its solubility in an aqueous biological fluid is difficult to deliver in meaningful amounts at controlled rates over time. The osmotic device of this patent comprises a semipermeable wall surrounding a compartment containing a beneficial agent that is insoluble to very soluble in an aqueous biological fluid and an expandable hydrogel. In operation, the hydrogel expands in the presence of external fluid that is imbibed into the device and in some operations mixes with the beneficial agents, thereby forming a dispensable formulation that is dispensed through the passageway from the device. This device operates successfully for its intended use, and it delivers many difficult to deliver beneficial agents for their intended purpose.

When administering a drug buccally (i.e., by absorption of the drug through the highly vascularized buccal tissues of the mouth) a number of conditions are present which makes it difficult to effectively deliver drug in a therapeutically effective amount for a prolonged period of time (e.g., for periods greater than several minutes). For example, when a patient is given a drug-containing lozenge, there is a natural tendency to suck and chew on the lozenge thereby effectively reducing the time period during which the drug can be buccally administered by the lozenge. In addition, the action of saliva and swallowing by the patient effectively reduces the concentration of drug along the buccal membranes of the oral cavity and further causes much of the drug to be swallowed, in many cases rendering it inactive upon encountering the low pH environment of the stomach. This has been a particular problem in treating diseases of the mouth which require constant local administration of drug. One such disease condition is candidiasis of the oral cavity. A recent study has shown that 94% of male patients having acquired immunodeficiency syndrome (AIDS) and 72% of those with AIDS-related complex (ARC) had oral candidiasis (Barr & Marder, AIDS: A Guide For Dental Practice, pp. 53–62, 1987). Recommended treatment of oral candidiasis is by continuous dosing of selected anti-fungal agents in the mouth, pharynx and oesophagus. Typically, therapeutically recommended doses of nystatin, amphotericin B or miconazole, either in the form of liquid rinses or slowly dissolving pastilles and tablets have been used to treat oral candidiasis. Unfortunately, when the anti-fungal agents are administered by gargling or with rinses, the anti-fungal agents are cleared from the mouth in a matter of minutes. While the duration of drug delivery is increased somewhat using slowly dissolving pastilles and tablets, typically these release drug for no more than about 15 to 20 minutes. Accordingly, these dosage forms require frequent repetitive dosing (e.g., gargling every five minutes or taking a lozenge 3–4 times per hour) in order to effectively treat the condition.

Another disease condition of the oral cavity for which continuous dosing of drugs has been recommended is in preventing the formation of plaque on teeth. Plaque is the non-calcified accumulation of microorganisms, which are naturally present in the mouth, and byproducts produced by the microorganisms. Plaque adheres tenaciously to the teeth and eventually gives rise to caries in the teeth and/or inflammatory changes in the buccal tissues adjacent the roots of teeth. Because of the bacterial origin of plaque, the drugs used to treat plaque formation have generally been antimicrobial agents such as chlorhexidine digluconate (PERIDEX sold by The Proctor & Gamble Co. of Cincinnati, Ohio); phenolic compounds such as thymol, menthol and eucalyptol (LISTERINE sold by Warner-Lambert Co. of Morris Plains, N.J.); benzophenathradine (VIADENT sold by Vipont Pharmaceutical, Inc. of Fort Collins, Colo.); triclosan and zinc citrate; stannous fluoride; and cetylpyridinium chloride (CEPA- COL sold by Marion Merrell Dow of Cincinnati, Ohio and SCOPE sold by The Proctor & Gamble Co. of Cincinnati, Ohio).

Thus, there has been a clear need in the art of treating oral diseases, such as plaque formation and oral candidiasis, for a dosage form which is able to continuously deliver therapeutically effective amounts of a drug or other beneficial agent into the oral cavity for extended periods of time, i.e. periods greater than about 15 to 20 minutes.

One proposed solution to the problem of short duration of drug delivery from rinses, pastilles, and tablets, has been a delivery device comprised of a hydrophilic polymer having a drug dispersed therein. When placed between the cheek and gum of a patient, the hydrophilic polymer absorbs moisture from the buccal membrane, eventually adhering itself to the membrane surface. While it is desirable from the standpoint of patient comfort and convenience to adhere the delivery platform directly to the buccal membrane, this can create a problem when delivering a drug having a tendency to cause irritation. When delivering an irritating drug, these devices tend to magnify the irritation since the device is adhered to the buccal membrane and maintains a high concentration of the irritating drug at a single membrane site.

Thus, there has been a need in the art of treating oral diseases for a dosage form which is able to continuously deliver a potentially irritating drug for extended periods of time without causing irritation.

Another proposed solution to the problem of short duration of drug delivery from rinses, pastilles and tablets, is the use of an osmotic pump to deliver medication to the buccal tissues. There are two broad categories of osmotic pumps: elementary osmotic pumps and osmotic pumps having an expandable push layer or material. Elementary osmotic pumps are typically formed by compressing a tablet of an osmotically active drug (or an osmotically inactive drug in combination with an osmotically active agent or osmagent) and then coating the tablet with a semipermable membrane which is permeable to an exterior aqueous-based fluid but impermeable to the passage of drug and/or osmagent. One or more delivery orifices may be drilled through the semipermeable membrane wall. Alternatively, orifice(s) through the wall may be formed in situ by incorporating leachable pore forming materials in the wall. In operation, the exterior aqueous based fluid is imbibed through the semipermeable membrane wall and contacts the drug and/or salt to form a solution or suspension of the drug. The drug solution or suspension is then pumped out through the orifice as fresh fluid is imbibed through the semipermeable membrane.

While the use of elementary osmotic pumps has proven to be very successful in delivering drugs through the GI tract (i.e., by swallowing the elementary osmotic pump), there are several problems with buccal administration. As with drug-containing lozenges, there is a natural tendency for the patient to suck and chew on the drug-containing elementary osmotic pumps. Chewing in particular tends to compress the deformable membrane wall, thereby squeezing the drug solution or suspension out of the device at an accelerated rate. The duration of drug delivery is therefore severely curtailed. For example, an elementary osmotic pump, originally designed to be swallowed and thereby deliver drug at a relatively constant rate over a period of 12 to 24 hours within the GI tract but which is instead placed in the oral cavity and subjected to patient sucking and chewing, delivers the entire drug dose relatively quickly, sometimes in less than about an hour.

More recently, Barclay et al. in U.S. Pat. No. 5,021,053 disclosed the use of an osmotic pump having an expandable hydrogel "push" layer to deliver medication to the buccal tissues. The Barclay et al. pumps used a gelling/suspending agent mixed into the drug-containing layer to internally support the semipermeable wall of the pump. The gelling agents used in the Barclay et al. pumps are generally water-soluble hydrogels, such as polyethylene oxides. Unfortunately, at least some of these hydrogel gelling/suspending agents are pumped out of the delivery orifice along with the drug. In the case of polyethylene oxides, this tended to give the patient a sticky or slimy mouthfeel.

Although Barclay et al.'s bilayer (i.e., (1) a drug- and gelling agent-containing layer and (2) a hydrophilic polymer push layer) osmotic device represented a significant improvement over the use of elementary osmotic pumps in the oral cavity, the natural tendency for patients to suck on the pump still resulted in premature drug release at least in part because the gelling/suspending agents were unable to withstand the pressures encountered during severe sucking and chewing. For example, in devices designed to deliver drug over a period of about 3 hours, patients who would agressively suck on the Barclay et al. pumps could decrease the duration of drug delivery by as much as 50% (i.e., drug was completely released in about 1.5 hours).

The problem of premature drug release becomes even more significant when using an osmotic pump designed to deliver a drug to the buccal tissues at a high dosage rate and with a minimum start-up time. Such pumps typically have a membrane wall which is extremely thin and porous. While such thin porous membranes are able to achieve the desired short start-up time and high pumping rates, they are extremely fragile and therefore especially susceptable to breaking (e.g., upon chewing) when placed in the oral cavity.

DISCLOSURE OF THE INVENTION

Accordingly, it is an object of this invention to provide an osmotic device for the controlled delivery of a beneficial agent to the oral cavity of an animal, and in particular a human, for an extended period of time.

It is another object of the invention to provide an oral osmotic device useful for delivering an agent into the mouth of a patient, which device has the ability to deliver drug into the oral cavity with a minimal start up time and at a relatively high pumping rate and yet which is not susceptable to premature release of drug due to patient sucking and chewing.

It is a further object of the invention to provide such a device which contains no water soluble and water expandable hydrophilic gel materials which, in the case of polyethylene oxide gels, gave the prior art devices a sticky or slimy mouthfeel.

Other objects, features, aspects and advantages of the invention will be more apparent to those versed in the art from the following detailed specification taken in conjunction with the figures and the accompanying claims.

This invention concerns an osmotic device for controlled delivery of a beneficial agent into the oral cavity of an animal, such as a human. The device has a size and shape allowing it to be comfortably retained in the oral cavity for an extended period of time. The device comprises a wall formed of a material which is permeable to the passage of an external aqueous fluid which is present in the oral cavity (e.g., saliva). The wall material may be either substantially impermeable or partially permeable to the passage of the active agent. The wall surrounds a solid dose of the beneficial agent which is in communication with the exterior of the device through one or more passageways in the wall. The solid dose comprises a beneficial agent exhibiting at least some degree of solubility, and preferably a high degree of solubility, in the aqueous fluid. The solid dose also includes a fibrous support material comprised of hydrophilic water-insoluble fibers. The wall material is substantially impermeable to the fibrous support material. The hydrophilic fibers absorb fluid (e.g., water) imbibed into the compartment, and expand slightly to form a rigid fibrous internal support for the semipermeable wall. Agent is released from the device by the fluid permeating through the semipermeable wall into the compartment producing a solution of the agent. As fresh fluid permeates through the wall, the agent solution is pumped out of the compartment through the passageway through the wall. The agent is released through the passageway at a rate primarily controlled by the fluid permeability of the wall and the osmotic pressure gradient across the wall.

BRIEF DESCRIPTION OF DRAWINGS

In the drawings (which are not drawn to scale) and the specification, like parts in related figures are identified by like numerals.

MODES FOR CARRYING OUT THE INVENTION

Figure 1:
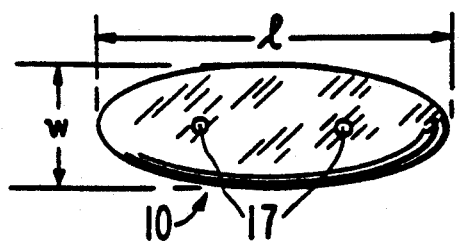
FIG. 1 is a top view of a preferred embodiment of an osmotic device for administering a beneficial agent into the oral cavity of an animal.
Figure 2:
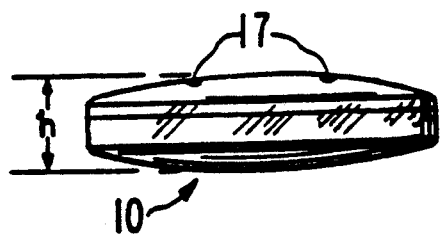
FIG. 2 is a side view of the oral osmotic device shown in FIG. 1.
Figure 3:
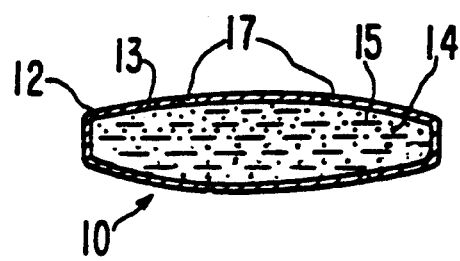
FIG. 3 is a side sectional view of the osmotic device of FIGS. 1 and 2.

Turning now to the Figures, one example of an oral osmotic device is shown in FIGS. 1 through 3, and is indicated by the numeral 10. Device 10 is comprised of a wall 12 that surrounds a tablet 13, as seen in the sectional view of FIG. 3. Tablet 13 contains a beneficial agent 14, that can be from insoluble to very soluble in an exterior aqueous fluid (i.e., saliva). When agent 14 is soluble in the exterior fluid, it exhibits an osmotic pressure gradient across wall 12 against the exterior fluid and the fluid thereby permeates through wall 12. Tablet 13 in another embodiment contains an agent 14 that has limited solubility or is substantially insoluble in the exterior fluid, and it exhibits a limited, or it may not exhibit any osmotic pressure gradient across wall 12 against the exterior fluid. When agent 14 has a limited solubility in the exterior fluid, it can be mixed with an osmagent that is soluble in the external fluid and exhibits an osmotic pressure gradient across wall 12 against the fluid. Wall 12 is formed of a polymeric material that is substantially permeable to the passage of the external fluid, and either impermeable or partially permeable to the passage of agent and osmagent. The polymer forming wall 12 is non-toxic and it maintains its physical and chemical integrity during the life of device 10.

In order to withstand the conditions of use within the oral cavity (i.e., patient sucking and chewing of the delivery device), tablet 13 contains a fibrous support material 15 comprised of hydrophilic water-insoluble fibers. The terms "fiber" and "fibrous" used herein refer not only to true fibers, including threads and hollow fibers, but also to materials made of fibers such as gauze, paper, braids, meshes, ribbons, bristles, rods, flakes, fibrous granules, fibrous aggregates and fiber-containing fabrics. The fibrous support material 15 can be made from either natural or synthetic hydrophilic water insoluble fibers. Natural hydrophilic water insoluble fibers include cotton, wool, silk and fibers from seed hulls. Synthetic hydrophilic water insoluble fibers include rayon, polyester, polyvinyl alcohol, polyacrylonitrile and cellulosic fibers. Tablet 13 contains from about 5 to 75 dry wt. %, and preferably from about 20 to 30 dry wt. % of the fibrous support material 15. The hydrophilic water insoluble fibers of material 15 generally have a nominal length of at least 5 microns, preferably at least 25 microns. Thus, wall 12 is substantially impermeable to the passage of the fibrous support material 15. As the external aqueous fluid permeates through wall 12, the hydrophilic fibers absorb a portion of the fluid and swell slightly. Once swollen, the fibers provide a relatively rigid internal support structure for the thin semipermeable wall 12. The rigid internal support structure renders the device 10 substantially incompressible under typical conditions of use in the oral cavity and thus prevents drug solution from being prematurely squeezed out of the device by patient chewing and sucking. In general, the devices of the present invention exhibit a buckling pressure (Pc) of at least about 100 mm Hg, and preferably at least about 200 mm Hg. The buckling pressure can be measured following the procedures described in Example 1.

Examples of hydrophilic water insoluble fibrous support materials include microcrystalline cellulose fibers (Avicel® PH 101, Avicel® PH 102, Avicel® PH 103, Avicel® PH 104, and Avicel® PH 105 and Avicel® large particle size 200, all sold by FMC of Philadelphia, Pa.) cellulose fibers (Emcocel® fibers; and Solka Floc ™ fibers in grades SW 40, BW 20, BW 40, BW 60, BW 100, BW 200, BW 300 and BW 20/30, all sold by Edward Mendell Co., Inc. of Carmel, N.Y.; and Elcema® fibers sold by Degussa AG, Germany); cellulose ester fibers; chitin and chitosan fibers; cross-linked sodium carboxymethylcellulose fibers (Ac-disol® ECG-505 fibers sold by FMC of Philadelphia, Pa. and Nymcel ZSB 10, Nymcel ZSB 16, and Nymcel ZSD 16 fibers all sold by Nyma of Nijmegen, Holland and CLD-2 fibers sold by Buckeye Cellulose Corp. of Memphis, Tenn.); low-substituted hydroxypropylcellulose fibers having a hydroxypropyl content of about 5-16 wt. % (such as LHPC 11, LHPC 20, LHPC 21, LHPC 22 AND LHPC 31 all sold by Shin-Etsu Chemical Co., Ltd. of Tokyo, Japan); soy bean fibers (such as Fibred FI-1 fibers sold by Fibred, Inc. of Cumberland, Md. and Emcosoy fibers sold by Edward Mendell Co., Inc.); seaweed fibers (such as alginic acid Satialgine H8 ™ fibers and calcium alginate Satialgine C, all sold by Edward Mendell Co., Inc.); blends of these, and the like.

Optionally, the hydrophilic water insoluble fibrous support material may be blended with one or more non-fibrous, hydrophilic, water insoluble materials to enhance the mechanical support properties of the fibrous support material. Examples of non-fibrous, hydrophilic, water insoluble additives include starch granules such as corn starch, rice starch, wheat starch, tapioca starch, sago starch and potatoe starch; starch-based derivatives such as sodium starch glycolate (Explotab ® sold by Edward Mendell Co., Inc.); mineral oxides such as silicon dioxide, ferric oxide, titanium dioxide; and synthetic granules such as cross-linked polyvinyl pyrrolidone (Polyplasdone ® XL and XL-10, both sold by GAF Corp. of Wayne, N.J.).

Device 10 releases agent 14 through one or more passageways 17 through wall 12. Device 10 releases agent 14 by an external fluid (e.g., saliva) permeating through wall 12 in a tendency towards osmotic equilibrium at a rate determined by the permeability of wall 12 and the osmotic pressure gradient across wall 12. The imbibed fluid continuously forms a solution of the agent 14, or in cases where the agent 14 has limited solubility in the external fluid, a solution of the osmagent and the agent 14, which solution in either instance is released by the operation of device 10. This operation includes the solution being osmotically delivered through passageways due to the continuous permeation of fresh external fluid through wall 12 and to a much smaller extent by the hydrophilic fibers in material 15 swelling and applying pressure against the solution thereby delivering it through passageways 17 to the exterior of device 10.

Device 10 of FIGS. 1-3 is designed for oral use, that is, for releasing either a locally or systemically acting therapeutic agent in the oral cavity of an animal, such as a human, over an extended period of time. Because the device is designed to be retained in the mouth for periods on the order of about 0.5 to 12 hours, the device must have an exterior shape which is comfortably retained in the mouth. It has been found that an oblong or elliptically shaped device 10 is preferred from a comfort standpoint. As shown in FIGS. 1 and 2, device 10 has a length l, a width w, and a height h. It has been found that devices 10 having an aspect ratio, which ratio is the ratio of l:w, of about 1.2:1 to about 3:1 are most comfortably retained in the mouths of humans. Preferably, the device 10 has an aspect ratio of about 1.3:1 to about 2:1, and most preferably about 1.5:1 to about 1.7:1. In addition, in order to fit comfortably between the cheek and gum of a patient, the device has a height of about 0.5 to about 10 mm, preferably about 2 to about 8 mm, and most preferably about 3 to about 5 mm. The device also has a volume of less than about 2 cm$^3$, preferably about 0.1 to about 0.5 cm$^3$, and most preferably about 0.25 cm$^3$.

Osmotic delivery device 10 can be manufactured with a wall 12 formed of a material that does not adversely affect the agent 14 (e.g., a drug), the osmagent, if any is present, and the fibrous support material 15. The material forming wall 12 should also not adversely affect the buccal tissues of the patient and should be insoluble in fluids naturally present in the oral cavity. In addition, the material forming wall 12 is permeable to the passage of an external aqueous fluid, such as water and biological fluids naturally present in the oral cavity (e.g., saliva), while remaining essentially impermeable to the passage of the fibrous support material and preferably impermeable to the passage of agents, including drugs, osmagents, and the like.

In accordance with a preferred embodiment of the present invention, wall 12 is comprised of a relatively high flux membrane material. The high flux membranes are useful when the device 10 is designed to deliver a relative large dose of drug (e.g., 200 to 500 mg) over a relatively short period of time (e.g., up to about 3 hours). Generally, high flux semipermeable membrane materials have a thickness of about 1 to 10 mils; a porosity of about 40 to 70 vol. %; and a fluid permeability greater than about $2 \times 10^{-4}$ cm mil/atm hr expressed per atmosphere of hydrostatic or osmotic pressure difference across semipermeable wall 12.

Typical materials for forming wall 12 include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminacetate, cellulose acetate ethyl carbamate, cellulose acetate chloracetate, cellulose dipalmatate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly(-sodium styrene sulfonate), poly(vinylbenzyltrimethyl ammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020.

The expression "active agent", as used herein includes any beneficial agent or compound, that can be delivered from the device into the oral cavity to produce a beneficial and useful result. The agent can be insoluble to very soluble in the exterior fluid. For example, the agent can be very soluble in the exterior fluid that enters compartment 13 and function as its own osmotically effective solute, or it can be poorly soluble in the fluid and be mixed with an osmotically effective compound that is soluble in the fluid for delivering an agent from the device.

In the specification and the accompanying claims, the term "agent" includes drug, and the term "drug" includes any physiologically or pharmacologically active substance that produces a local or systemic effect when administered to the oral cavity of a human. The term "physiologically" as used herein denotes the administration of a drug to produce normal levels and functions. The term "pharmacologically" denotes variations in response to amount of drug administered to the host. *Stedman's Medical Dictionary*, 1966, published by Williams and Wilkins, Baltimore, Md. The active drug that can be delivered includes inorganic and organic drugs without limitations, those drugs that act on the central nervous system, depressants, hypnotics, sedatives, psychic energizers, tranquilizers, anticonvulsants, muscle relaxants, antiparkinson agents, analgesics, anti-inflammatory drugs, local anesthetics, muscle contractants, anti-plaque agents, anti-microbials, anti-fungals, anti-malarials, hormonal agents, contraceptives, sympathomimetics, diuretics, anti-parasitics, neoplastics, hypoglycemics, ophthalmics, electrolytes, diagnostic agents, and cardiovascular drugs.

Because the osmotic device of the present invention is designed for use in the oral cavity, it is particularly suited for delivering anti-plaque agents. Suitable anti-plaque agents having good water solubility, or which can be rendered water soluble by appropriately adjusting their pH, include chlorhexidine salts such as clorhexidine digluconate, chlorhexidine dichloride and chlorhexidine diacetate, cetylpyridinium chloride, ethanol, sodium salicylate, sodium borate, sodium benzoate, dequalinium chloride, benzalkonium chloride, aminacridine hydrochloride, mepacrine hydrochloride, peroxides such as hydrogen peroxide and potassium peroxidiphosphate, proguanil hydrochloride, dibromopropamidine diisothionate, pyrimidine derivatives such as hexidine, alexidine, octenidine, plant alkaloids such as sanguinarine and sanguinarine chloride, metal salts such as zinc citrate, non-charged phenolic agents such as thymol and triclosan, enzyme systems such as mutanases, amylogycosidase and glucose-oxidase, sugar substitutes such as xylitol and mannitol, fluorides such as stannous fluoride and sodium fluoride, surface modifying agents such as decapinol, sodium polyvinylphosphonic acid, perfluoroalkyl surfactants and cetyldimethylbenzyl ammonium chloride.

Other exemplary drugs that are very soluble in water and can be delivered by the devices of this invention include nystatin, clonidine, prochlorperazine adisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, salbutanol hemisulfate, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metoprolol tartrate, cimetidine hydrochloride, nitroglycerin, and the like.

Exemplary drugs that have a low solubility in water and that can be delivered by the devices of this invention include nicotine base, retin A, ibuprofen, insulin, diphenidol, meclizine hydrochloride, prochlorperazimine maleate, phenoxybenzamine, thiethylperazine maleate, anisindone, diphenadione erythrityl tetranitrate, dizoxin, isofuraphate, reserpine, acetazolamide, methazolamide, bendroflumethiazide, chlorpropamide, tolzamide, chlormadinone acetate, phenaglycodol, allopurinol, aluminum aspirin, methotrexate, acetyl sulfisoxazole, erythromycin, progestins, esterogenic progestational hormones, corticosteroids, hydrocortisone, hydrocorticosterone acetate, cortisone acetate, triamcinolone, testosterone, testosterone esters, methyltesterone, 17β-estradiol, ethinyl estradiol, ethinyl estradiol 3-methyl ether, prednisolone, 17β-hydroxyprogesterone acetate, 19-nor-progesterone, norgestrel, norethindone, norethiderone, progesterone, norgesterone, norethynodrel, isosorbide dinitrate, and the like.

Examples of other drugs that can be delivered by the osmotic device include aspirin, indomethacin, naproxen, fenoprofen, sulidac, diclofenac, indoprofen, nitroglycerin, propranolol, metoprolol, valproate, oxprenolol, timolol, atenolol, alprenolol, cimetidine, clonidine, imipramine, levodopa, chlorpromazine, methyldopa, dihydroxyphenylalanine, pivaloyloxyethyl ester of α-methyldopa hydrochloride, theophylline, calcium gluconate, ferrous lactate, vincamine, diazepam, phenoxybenzamine, α-blocking agents, polypeptides, proteins, insulin and the like. Other beneficial drugs are known to the art in *Pharmaceutical Sciences*, by Remington 14th Ed., 1979, published by Mack Publishing Co., Easton, Pa.; *The Drug, The Nurse, The Patient, Including Current Drug Handbook*, 1974–1976, by Falconer, et al., published by Saunders Company, Philadelphia, Pa.; and *Medicinal Chemistry*, 3rd Ed., Vol. 1 and 2, by Burger, published by Wiley-Interscience, New York.

The drug can be in various forms, such as uncharged molecules, molecular complexes, pharmacologically acceptable salts such as hydrochloride, hydrobromide, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. Drugs in the form of polypeptides and proteins, which are susceptible to being broken down in the GI tract, can also be delivered systemically by the device of the present invention by absorption through the buccal membranes of the oral cavity.

The tablet 13 may also contain convention tableting excipients including binders, dyes, dispersants, wetting agents and lubricants. Representative of these include binders like polyvinyl pyrrolidone, and hydroxypropyl methyl cellulose, wetting agents such as fatty amines and fatty quaternary ammonium salts, and lubricants such as magnesium stearate and stearic acid.

The amount of agent initially present in the device is not critical, however it is preferred to initially provide an amount of active agent, which agent is soluble in fluid entering the device, in excess of the amount that can be dissolved in the fluid that enters the device. Under this physical state, when the agent is in excess, the device will osmotically operate to give a substantially constant rate of release. Generally, the device can house from about 0.05 ng to 500 mg or more of drug, carrier, fillers, excipients, etc. with individual devices containing for example, 25 ng, 1 mg, 5 mg, 125 mg, 250 mg, 500 mg, and the like.

The osmagent present in the device, when used according to the mode of the invention where the beneficial agent has poor aqueous solubility, are osmotically effective compounds soluble in the fluid that enters the device, and exhibits an osmotic pressure gradient across the semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, xylitol, inositol, raffinose, sucrose, glycose, hydrophilic polymers such as cellulose polymers, mixtures thereof, and the like. The osmagent is usually present in an excess amount, and it can be in any physical form, such as particle, powder, granule, and the like. The osmotic pressure in atmospheres of the osmagents suitable for the invention will be greater than zero and generally up to about 500 atm, or higher.

For the purpose of the invention, the phrase agents with degrees of solubility as used herein indicates agents that have at least some degree of solubility in aqueous biological fluids present in the oral cavity, such as saliva. Further for this purpose, an agent having a low degree of solubility is one that dissolves in the range of about 25 mg to 150 mg of agent per ml of fluid, whereas an agent having a high degree of solubility dissolves greater than about 150 mg of agent per ml of fluid.

Typical methods used for the measurement of solubility are chemical and electrical conductivity. Details of various methods for determining solubilities are described in *United States Public Health Service Bulletin,* No. 67 of the Hygienic Laboratory; *Encyclopedia of Science and Technology,* Vol. 12, pages 542 to 556, 1971, published by McGraw-Hill, Inc,; and *Encyclopedia Dictionary of Physics,* Vol. 6, pages 547 to 557, 1962, published in Pergamon Press, Inc.

The device of the invention is manufactured by standard techniques. For example, in one embodiment, the agent, the fibrous support material, and other optional ingredients can be simply mixed into a solid or semisolid form by conventional methods such as ballmilling, calendering, stirring or rollmilling, and then pressed into a preselected shape using a conventional tableting press. The wall 12 can be applied by molding, spraying or dipping the pressed shapes into a wall forming material. Another and presently preferred technique that can be use for applying the wall is the air suspension procedure. This procedure consists of suspending and tumbling the pressed agent and dry hydrophilic polymer in a current of air and a wall forming composition until the wall is applied to the agent fibrous support material composite. The air suspension procedure is described in U.S. Pat. No. 2,799,241; *J. Am. Pharm. Assoc.,* vol. 48, pages 451 to 459, 1979; and ibid. Vol. 49, pages 82 to 84, 1960. Other standard manufacturing procedures are described in *Modern Plastics Encyclopedia,* Vol. 46, pages 62 to 70, 1969; and in *Pharmaceutical Sciences,* by Remington, Fourteenth Edition, pages 1626 to 1678, 1970, published by Mack Publishing Company, Easton, Pa.

Exemplary solvents suitable for manufacturing the wall include inorganic and organic solvents that do not adversely harm the wall forming material, and the final device. The solvents broadly include members selected from the group consisting of aqueous solvents, alcohols, ketones, esters, ethers, aliphatic hydrocarbons, halogenated solvents, cycloaliphatic, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglycol methyl ether, water and mixtures thereof such as acetone and water, acetone and methanol, acetone and ethyl alcohol, methylene dichloride and methanol, and ethylene dichloride and methanol, and mixtures thereof.

The expression "passageway" as used herein comprises means and methods suitable for releasing the agent from the device. The expression includes one or more aperture, orifice or bore through wall 12 formed by mechanical procedures, or by eroding an erodible element, such as a gelatin plug, in the oral cavity. In cases where the semipermeable membrane is sufficiently permeable to the passage of beneficial agent/drug, the pores in the membrane may be sufficient to release the agent/drug in therapeutically effective amounts. In such cases, the expression "passageway" refers to the pores within the membrane wall even though no bore or other orifice has been drilled therethrough. A detailed description of osmotic passageways and the maximum and minimum dimensions for a passageway are disclosed in U.S. Pat. Nos. 3,845,770 and 3,916,899, the disclosures of which are incorporated herein by reference. Preferably, 1 to 2 passageways 17 are provided in device 10 as shown in the Figures.

The expressions "extended period of time" and "extended delivery period" as used herein generally refers to periods greater than about 0.5 hours, preferably about 0.5 to 12 hours, more preferably about 0.5 to 6 hours, most preferably about 1-4 hours.

The following examples are merely illustrative of the present invention and should not be considered as limiting the scope of the invention in any way.

EXAMPLE 1

An osmotic therapeutic device was made for the controlled and continuous release into the oral cavity of the beneficial antimicrobial drug cetylpyridinium chloride (CPC) sold by Spectrum Chemical Manufacturing Corp., Gardena, Calif. The following components were pre-sieved #40 mesh and dry mixed: 37 g sorbitol, 5 g low-substituted hydroxypropyl cellulose fibers having a nominal length of 50 microns (LHPC 11 sold by Shin-Etsu Chemical Co., Ltd.of Tokyo, Japan) and 5 g microcrystalline cellulose fibers having a nominal length of 200 microns (Avicel ® PH 102 sold by FMC of Philadelphia, Pa.). Then 1.5 g CPC was dissolved in 30 ml ethanol SDA, anhydrous. The drug solution was stirred into the pre-mix to form a uniform, doughy mass. The resulting dough was passed through a #20 mesh sieve, forming damp granules. These granules were air dried overnight, then re-passed through the #20 mesh sieve. Then 1.5 g TWEEN 80 was blended into the granulation.

200 mg portions of this granulation were compressed in a ¼ inch oval tablet tooling at 2 tons pressure. The resulting compressed cores were then coated with about 50 mg of a 50/50 wt % mixture of cellulose acetate (cellulose acetate 398-10 sold by Eastman Chemical Products, Inc. of Kingsport, Tenn.) and polyethylene glycol (Carbowax ® PEG 3350 sold by Union Carbide Corp. of Danbury, Conn.) deposited from a 95/5 wt. % acetone and water solution. The coated systems were air dried overnight. Then, two 15 mil diameter exit ports were drilled, one port per side.

Figure 4:
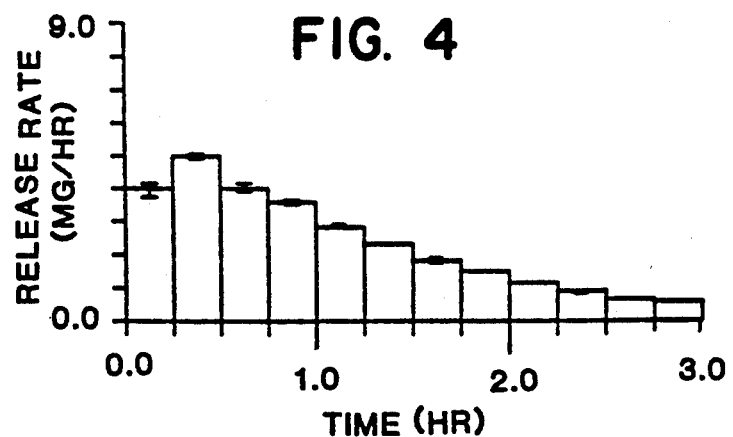
FIG. 4 is a graph depicting the beneficial agent release rate of an osmotic device according to the present invention.

The systems were immersed in artificial intestinal fluid for three hours to determine their in vitro release rate. The systems uniformly released their contents as shown by the gradually declining bar graph in FIG. 4. When tested in the oral cavity, the systems released similarly to this in vitro release pattern, i.e., the duration of drug delivery was also about three hours.

The artificial intestinal fluid was made by dissolving 6.8 g of monobasic potassium phosphate in 150 ml water and adding 190 ml of 0.2N sodium hydroxide. The pH of the artificial intestinal fluid was adjusted to 7.5 using the sodium hydroxide.

The buckling pressure of spent, hydrated systems was measured as follows. Four vent holes were mechanically pierced through the lateral edge of the membrane with a 22 gauge needle. The outside diameter of the needle was 0.028 inch. The holes were spaced evenly at 90 degree intervals around the lateral edge of the membrane. The system was then wrapped in a single layer of nylon mesh netting (20 holes per inch of mesh). A small vent tube (inside diameter of 0.027 inch, outside diameter of 0.42 inch) was placed near one of the vent holes through a slit in the mesh. The resulting assembly was then sandwiched between two latex sheets (0.002 inch thick) which were mounted in a bi-chamber pressure cell. The vent tube was oriented such that it was exposed to ambient atmospheric pressure. The chambers shared a common source of pressurized air and the air pressure within the chambers was monitored with a manometer.

Compressed air was forced into the chambers causing pressure on the latex sheets. This pressure in turn squeezed the spent system. As the air pressure in the chambers was gradually increased, the fluid within the spent system was squeezed from the system through the vent tube to the atmosphere. The pressure at which the membrane shell could no longer retain its shape and collapsed was recorded in millimeters of mercury. The buckling pressure of the spent systems consistently exceeded 400 mm Hg.

COMPARATIVE EXAMPLE 1

When comparable systems to those described in Example 1, but without any low substituted hydroxypropyl cellulose or microcrystalline cellulose fibers in the core, were tested in the oral cavity, release of a drug was prone to uncontrolled mechanical pumping and convective losses with the CPC being completely released within 30 minutes. The buckling pressures of the spent systems of Comparative Example 1 were less than 199 mm Hg.

EXAMPLE 2

An osmotic, therapeutic device for continuous delivery of cetyl pyridinium chloride (CPC) and having a drug overcoating for instantaneous release of CPC in the oral cavity, was made as follows. The following components were pre-sieved on a #40 mesh sieve and dry mixed: 68.5 g sorbitol, 10 g LHPC 11, 10 g Avicel PH 102. Then, 3.3 g CPC was dissolved in ethanol and the solution was stirred into the pre-mix to form a uniform doughy mass. The resulting mass was passed through a #20 mesh sieve forming damp granules. These granules were air dried overnight, then repassed through the #20 mesh sieve. Then, 3.0 g TWEEN 80 and 5.0 g of a mint flavoring agent, was stirred into the granulation.

250 mg portions of this granulation were compressed with ⅜ inch oval tablet tooling and then coated with a 50/50 wt. % mixture of cellulose acetate 398-10 and PEG 3350 following the same procedure as described in Example 1. Then, two 15 mil diameter exit ports were drilled, one port per side. The systems were then each overcoated with 34 mg of an instant release overcoat layer. The overcoat layer was comprised of 13 wt. % CPC, 52 wt. % HPMC 603, 7 wt. % PEG 3350, 13 wt % TWEEN 80 and 14 wt. % of flavoring agents, e.g., mint flavor and sodium saccharin. The mint flavor was dispersed in water for 30 minutes. Then, TWEEN 80 was mixed in for 5 minutes, followed by the sodium saccharin, mixed for another 5 minutes. The CPC was added, and the mixture is stirred another 5 minutes. The PEG was added, mixed for 5 minutes, then the HPMC was added and the resulting blend was stirred for 1 hour. The final blend consisted of 14%/86% solids/purified water on a weight basis.

This coating fluid was applied to the drilled, membrane coated systems in a pharmaceutical coater using a stream of warmed air. The inlet temperature was approximately 70°-75° C. and the outlet temperature was approximately 38°-42° C. The resulting drug-overcoated systems were dried to constant weight.

Figure 5:
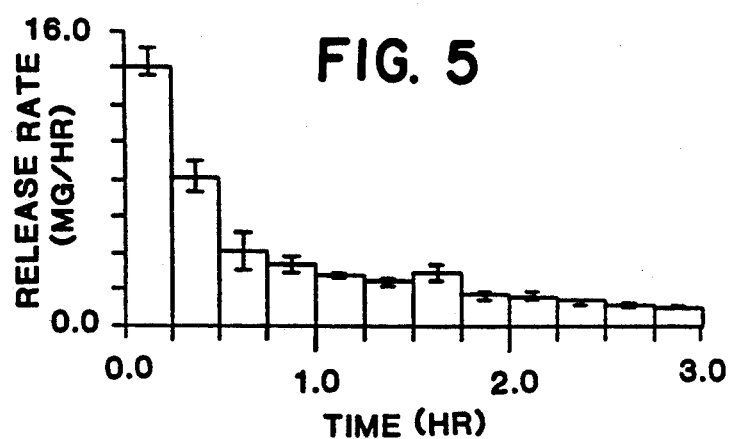
FIG. 5 is a graph depicting the beneficial agent release rate of an osmotic device having a loading dose.

The average release rates for these systems is illustrated in FIG. 5. The release rates were determined by immersing the systems in artificial intestinal fluid in accordance with the procedures described in Example 1. The high release rates recorded for the first 30 minutes of operation was due primarily to the CPC-containing overcoat layer, which dissolved very rapidly. The systems exhibited a relatively uniform pumping rate from 30 minutes until 3.0 hours following immersion in the intestinal fluid.

EXAMPLE 3

The following components were pre-sieved #40 mesh and dry mixed: 15 grams captopril, 64 grams sorbitol, 10 grams low-substituted hydroxypropyl cellulose fibers (hydroxypropoxy content 11 weight percent), and 10 grams cellulose fiber Solka-floc BW 40. After a uniform mixture was obtained, 1 gram of stearic acid sized to minus #80 mesh, was tumble mixed into the blend. Portions of the blend weighing 167 mg were compressed with a ⅜ inch by 3/16 inch oval tablet press. The resulting tablets were coated with a membrane composition consisting of 50% cellulose acetate having an acetyl content of 39.8 weight percent and 50% polyethylene glycol molecular weight 8.000 grams per mole. This membrane was sprayed from a solvent system of 95/5 acetone/water weight by weight in a pharmaceutical coating pan. After coating, the systems were dried to remove residual solvent. Then two 15 mil ports, one on each side of the system, were drilled. The resulting systems were given to patients who were asked to keep the system beneath their tongue (i.e., sublingual delivery). The systems provided controlled delivery and absorption of 25 milligrams captopril at an average rate of delivery of 6 mg captopril/hr. for a period about 4 hours for treatment of hypertension.

While there have been described and pointed out features of the invention as applied to the presently preferred embodiments, those skilled in the art will appreciate that various modifications, changes, additions and omissions in the systems illustrated and described can be made without departing from the spirit and scope of the invention as defined in the appended claims.

We claim:

1. An osmotic device for the controlled delivery of a beneficial agent to an oral cavity of an animal over an extended delivery period, the device having a size and shape suitable for comfortably retaining the device in the oral cavity for the extended delivery period, the device including a wall surrounding a solid dose of the beneficial agent, the beneficial agent exhibiting at least some degree of solubility in an aqueous fluid present in the oral cavity, and a fibrous support material comprised of hydrophilic water-insoluble fibers selected from the group consisting of cellulose fibers, microcrystalline cellulose fibers, cellulose ester fibers, crosslinked sodium carboxymethyl cellulose fiber, low-substituted hydroxypropyl cellulose fibers, seaweed fibers, chitin fibers, chitsan fibers, and blends thereof, the wall having a passageway communicating the solid dose with the exterior of the device, the wall being formed of a semipermeable material which is (i) permeable to the passage of the aqueous fluid and (ii) substantially impermeable to the passage of the fibrous support material.

2. The osmotic device of claim 1, wherein the solid dose contains an amount of the fibrous support material sufficient to impart a buckling pressure of at least about 100 mm Hg during use.

3. The osmotic device of claim 1, wherein the solid dose contains about 5 to 70 vol % of the fibrous support material.

4. A method for controlled delivery of a beneficial agent into an oral cavity of an animal over an extended delivery period, comprising:
  a) placing in the oral cavity of the animal an osmotic device having a size and shape suitable for comfortably retaining the device in the oral cavity for the extended delivery period, the device including a shaped semipermeable wall surrounding a solid dose of a beneficial agent that exhibits at least some degree of solubility in an aqueous fluid present in the oral cavity, a fibrous support material comprising hydrophilic water-insoluble fibers, and a passageway in the semipermeable wall connecting the exterior of the device and the agent for delivering the agent from the device into the oral cavity at a controlled rate over the extended delivery period, the wall being permeable to the passage of the aqueous fluid and substantially impermeable to the passage of the fibrous support material;
  b) allowing the aqueous fluid present in the oral cavity to permeate through the semipermeable wall to form a liquid solution of the beneficial agent; and
  c) delivering the solution of the beneficial agent into the oral cavity over the extended delivery period.

5. The osmotic device of claim 1, wherein the device exhibits a buckling pressure of greater than about 200 mm Hg during use.

6. The osmotic device of claim 1, wherein the semipermeable wall has a fluid permeability of greater than about $2 \times 10^{-4}$ cm.mil/atm.hr.

7. The osmotic device of claim 1, wherein the semipermeable wall has a thickness in the range of about 1 to 10 mils and a porosity of about 40 to 70 vol. %.

8. The osmotic device of claim 1, wherein the semipermeable wall has an overcoating containing beneficial agent.

9. The osmotic device of claim 1, wherein the device has a smooth oval shape with an aspect ratio in the range of about 1.2:1 to about 3:1, a height of about 0.5 to about 10 mm, and a volume of less than about 2 cm$^3$.

10. The osmotic device of claim 1, wherein the beneficial agent has a low degree of solubility in the aqueous fluid and the compartment also contains an osmagent.

11. The osmotic device of claim 1, wherein the device is substantially free of any gelling agent.

12. The osmotic device of claim 1, wherein the beneficial agent is a member selected from the group consisting of anti-plaque agents, antifungal agents, antiviral agents, antimicrobial agents, antibiotics, non-steroidal anti-inflammatory agents, anti-dental caries agents, saliva-enhancing agents, smoking cessation agents, oral ulcer healing agents and breath fresheners.

13. The osmotic device of claim 12, wherein the beneficial agent comprises an anti-plaque agent selected from the group consisting of clorhexidine digluconate, chlorhexidine dichloride, chlorhexidine diacetate, cetylpyridinium chloride, ethanol, sanguinarine, sanguinarine chloride, sodium salicylate, sodium borate, sodium benzoate, dequalinium chloride, benzalkonium chloride, aminacridine hydrochloride, mepacrine hydrochloride, hydrogen peroxide, potassium peroxidiphosphate, proguanil hydrochloride, dibromopropamidine diisothionate, hexidine, alexidine, octenidine, zinc citrate, thymol, triclosan, mutanases, amylogycosidase, glucose-oxidase, xylitol, mannitol, stannous fluoride, sodium fluoride, decapinol, sodium polyvinylphosphonic acid, perfluoroalkyl surfactants and cetyldimethylbenzyl ammonium chloride.

14. The method of claim 4, wherein the extended delivery period is about 0.5 to 12 hours.

15. The method of claim 4, wherein the extended delivery period is about 1 to 6 hours.

16. The method of claim 4, wherein the extended delivery period is about 1 to 4 hours.

17. The method of claim 4, wherein the beneficial agent is an anti-plaque agent which is administered to suppress the formation of plaque on teeth.

18. The method of claim 17, wherein the anti-plaque agent is selected from the group consisting of clorhexidine digluconate, chlorhexidine dichloride, chlorhexidine diacetate, cetylpyridinium chloride, ethanol, sanguinarine, sanguinarine chloride, sodium salicylate, sodium borate, sodium benzoate, dequalinium chloride, benzalkonium chloride, aminacridine hydrochloride, mepacrine hydrochloride, hydrogen peroxide, potassium peroxidiphosphate, proguanil hydrochloride, dibromopropamidine diisothionate, hexidine, alexidine, octenidine, zinc citrate, thymol, triclosan, mutanases, amylogycosidase, glucose-oxidase, xylitol, mannitol, stannous fluoride, sodium fluoride, decapinol, sodium polyvinylphosphonic acid, perfluoroalkyl surfactants and cetyldimethylbenzyl ammonium chloride.

19. The method of claim 17, wherein the anti-plaque agent comprises cetylpyridinium chloride.

* * * * *